United States Patent [19]

Bird et al.

[11] Patent Number: 4,869,017

[45] Date of Patent: Sep. 26, 1989

[54] MACROALGAE CULTURE METHODS

[75] Inventors: Kimon T. Bird, Vero Beach, Fla.; Rolland D. Carlson, Palatine, Ill.

[73] Assignee: Harbor Branch Oceanographic Institution, Inc., Ft. Pierce, Fla.

[21] Appl. No.: 55,339

[22] Filed: May 29, 1987

[51] Int. Cl.$^4$ .............................................. A01G 33/00
[52] U.S. Cl. ...................................... 47/1.4; 435/257
[58] Field of Search ................ 435/257; 423/164, 165; 47/1.4

[56] References Cited

PUBLICATIONS

C. A. Neyra, ed., Biochemical Basis of Plant Breeding, vol. 1, Carlson Metabolism, CRC Press, Inc., Boca Raton. Fla., 1985, p. 93.

Salesburg et al. (1985), Plant Physiology, Third ed., Wadsworth Publ. Co., Belmont, CA, p. 224.

J. McLachlan in *Handbook of Phycological Methods*, J. R. Stein, ed., (1973), Cambridge Univ. Press, Cambridge, pp. 25-51.

C. H. Sorum, (1964), *Fundamentals of General Chemistry*, Prentice-Hall, Inc., New Jersey, p. 500.

Daniels et al. (1967), *Physical Chemistry*, Third Edition, John Wiley and Sons, Inc., N.Y., pp. 140-141.

Lucas et al. (1985) Physcol. Plant., 65: 539-543.

*Primary Examiner*—Charles F. Warren
*Assistant Examiner*—Charles E. Cohen
*Attorney, Agent, or Firm*—Carroll F. Palmer

[57] ABSTRACT

Production of macroalgae, e.g., Gracilaria, in a marine culture system is enhanced by improving the manner in which the aqueous culture medium is created, namely, first adjusting the alkalinity of a quantity of freshwater by the addition of an alkaline reagent thereto, diluting seawater with such alkalinity adjusted freshwater to create a saline solution having a salinity of between about 15 to 25 parts per thousand and an alkalinity of between about 3 to 10 meq/l., dissolving carbon dioxide in the resulting solution to bring its pH to between about 7.5 and 8.5, and using such carbon dioxide enriched solution as the culture medium.

6 Claims, No Drawings

MACROALGAE CULTURE METHODS

BACKGROUND OF THE INVENTION

1. Field of the Invention

This invention relates generally to algae culture methods. More particularly, it concerns improvements in the culturing of macroalgae in marine media so as to enhance productivity and decrease operating costs of such operations.

2. Description of the Prior Art

Algae are cultured for a variety of purposes, e.g., as a source of agar, to provide fodder for animal and fowl feeding, etc. In such culture operations, dissolved carbon n the forms of carbon dioxide and/or bicarbonate may be growth limiting for large scale cultivation of significant marine macroalgae. In addition, the culture seawater may not have the capacity to dissolve all the $CO_2$ and bicarbonate the algae are capable of utilizing.

Current technology in macroalgae cultivation in ponds or raceways is performed under carbon limitation conditions, with attempts to overcome this typically by adding $CO_2$ into seawater charged into the culture system or by bubbling it directly into the culture medium. Adjustment of pH is often used to increase the concentration of the dissolved $CO_2$ and bicarbonate. However, such procedure still limits the amount of dissolved carbon available to consumption by the algae. In order to raise the carbon concentration capacity of seawater, the alkalinity must be raised, but direct addition of an alkaline reagent, e.g., NaOH, causes precipitation of important seawater ions, e.g., calcium or valuable nutrients such as nitrates and phosphates.

The present invention provides improvements in macroalgae cultivation though a technique for enhancing dissolved carbon concentrations in marine macroalgal culture systems.

OBJECTS

A principal object of the invention is the provision of improvements in the culturing of macroalgae in marine media so as to enhance productivity of such operations.

Further objects include the provision of:

1. Improved methods for the production of marine macroalgal culture media.

2. A combination of steps for the generation of marine solutions having enhanced dissolved carbon concentrations, particularly carbon dioxide and bicarbonate, that may be used a media in which to cultivate macroalgae.

3. A technique for increasing the concentration of dissolved carbon in marine solutions, particularly carbon dioxide and bicarbonate.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

The objects are accomplished, in part, in accordance with the invention by the provision of an improved method for the production of macroalgae in a marine culture system including, as a culture medium, an aqueous solution formed partially of seawater and containing dissolved carbon dioxide and dissolved bicarbonate at a predetermined pH.

The improvement involves the manner of creating the culture medium which comprises adjusting the alkalinity of a quantity of freshwater to between about 1 to 10 meg/l. by the addition of an alkaline reagent thereto, diluting seawater with the alkalinity adjusted freshwater to create a saline solution having a salinity of between about 15 to 25 parts per thousand and an alkalinity of between about 3 to 10 meq/1., dissolving carbon dioxide in the resulting solution to bring its pH to between about 7.5 and 8.5, and using the carbon dioxide enriched solution as the culture medium.

The objects are further accomplished by new methods for macroalgae cultivation which comprise the steps of forming a marine medium in which to conduct the culturing by diluting seawater with freshwater to a salinity of between about 15 to 25 parts per thousand, adjusting the pH of the marine medium to a pH of between about 7.5 and 8.5 and the alkalinity to between about 3 and 10 meq/1. by the addition of an alkaline reagent, dissolving carbon dioxide in the resulting adjusted marine medium, charging the carbon dioxide enriched marine medium into a containing space, inoculating the charged marine medium with macroalgae of the species to be cultured, and then permitting the inoculated marine medium to be exposed to sunlight whereby to grow the macroalgae species therein with enhanced productivity.

DESCRIPTION OF THE PREFERRED EMBODIMENTS

In accordance with this invention, a quantity of freshwater is first made alkaline using one, or a mixture of alkaline reagents, e.g., KOH, NaOH, $Na_2CO_3$. The quantity of the alkaline reagent to be used is calculated based on the desired alkalinity of a marine solution to be formed by diluting a specific quantity of seawater with a specific quantity of the alkaline adjusted freshwater. For making such calculation, the salinity and alkalinity of the seawater to be used in forming the marine solution is predetermined. Typical values for ocean water at 25° C would be, for example, a salinity of 33 parts per thousand by weight (ppt.), and alkalinity of 2.2 milliequivalents per liter (meg/l) and a pH of 8.3.

In preferred operations according to the invention, the salinity of the seawater will be reduced to between about 15 and 25 ppt. and its alkalinity will be increased to between about 3 and 10 meq/1 by admixture with the alkaline adjusted freshwater. The selection of the final alkalinity involves consideration of the desired total inorganic carbon concentration.

By way of example, a volume of freshwater, e.g., well water, steam plant condensate, wastewater treatment plant effluent, etc., is made to have an alkalinity of 18 meq/l. by the addition of NaOH. This is then mixed with an equal volume of ocean water to produce a marine solution having a salinity of 17 ppt. and an alkalinity of 10 meq/l.

Carbon dioxide is then dissolved in this marine solution in a closed vessel (to prevent outgassing) until a desired pH between about 7.5 and 8.5 is reached in the solution The selection of desired pH sets the ratio of different forms of dissolved carbon as $CO_2$, bicarbonate and carbonate and depends on a number of factors including the best pH for optimum crop yield or product yield, economics of the product and preferance of the organism for $CO_2$ or bicarbonate.

The resulting carbon enriched marine solution is then charged into a terrestrial pond or equivalent containing space, e.g., concrete tank, metal tank, etc., via a pH metering system to ensure the overall pond pH is maintained within the desired range. Since alkalinity is a biologically conservative factor (little affected by biological processes), alkalinity will remain high throughout the pond. High dissolved carbon concentrations can also be maintained at carbon adjustment stations by pH controllers placed at selected locations around the point where a fine sparge of $CO_2$ is injected directly into the pond. Alternatively, dissolved carbon adjustment can be made by further charging of carbon enriched influent.

If the pond is newly formed, it will be inoculated with the specie of macroalgae to be cultivated, but if the charging of the marine solution is to an old culture system, this is not necessary. In any event, the pond will then be exposed to sunlight to grow the macroalgae at enhanced levels of productivity.

The enhanced level of dissolved carbon attainable by the new procedures for producing marine culture media according to the invention cannot be realized by simple dilution of seawater with freshwater and direct addition of alkali thereto to increase alkalinity. Thus, dilution without alkalinity control has been found not to significantly improve the attainable concentrations of dissolved carbon in the saline culture solutions as shown by the following table

TABLE 1

| Value | A | B | C | D |
|---|---|---|---|---|
| salinity (ppt.) | 33 | 17 | 17 | 17 |
| alkalinity (meq/l.) | 2.3 | 2.3 | 10 | 10 |
| pH | 8.3 | 8.3 | 8.3 | 7.5 |
| Temp.° C. | 25 | 25 | 25 | 25 |
| mM dissolved C | 1.93 | 2.09 | 9.22 | 10.22 |
| mM $CO_2$ | 0.0085 | 0.012 | 0.52 | 0.38 |
| mM bicarbonate | 1.67 | 1.90 | 8.37 | 9.70 |
| mM carbonate | 0.26 | 0.18 | 0.78 | 0.14 |

In Table 1, solution A is a typical unadjusted seawater saturated with $CO_2$ to the extent that normal alkalinity will permit. Solution B is seawater diluted with an equal volume of freshwater and saturated with $CO_2$. Solution C is the marine culture solution whose production is described above. Solution D shows the effect on carbon content with lowered pH, i.e., increase in bicarbonate.

Direct addition of alkali to seawater to increase alkalinity causes a strong precipitation of Mg and Ca salts. Initially diluting the seawater and then adding alkali directly also eventually reduces the amount of alkalinity due to Ca and Mg salt precipitation. On the other hand, prior dissolution of alkali salt in freshwater allows one to produce an alkaline medium which can be used to dilute seawater to a lower salinity without precipitation. Acting in accordance with the invention, it has been found possible to produce diluted seawater with a salinity of 17 ppt. and an alkalinity of 10 meq/l. without a precipitation problem.

As such, the invention produces a diluted seawater with enhanced dissolved carbon concentration. The fact that macroalgae, e.g., Gracilaria, exhibit improved photosynthesis and, in turn, productivity, at higher dissolved carbon as compared to growth in seawater, makes it possible to obtained substantially improved yield of algae for a given culture volume and time.

The improvements of the invention are significant for macroalgae as compared to microalgae because macroalgae can be fertilized with high concentrations of dissolved nutrients, such as nitrates and phosphates in normal seawater, for 24 hour periods followed by flushing and renewal of carbon enrichment. Macroalgae can store these nutrients and use them for growth for a period of 1-2 weeks. Nutrient storage by microalgae, in contrast, is on the order of 1-2 days, if at all. Therefore, microalgae must continually receive nutrients in the culture medium, but prolonged retention of high alkalinity in the medium causes precipitation problems of these N and P nutrients. The long term nutrient storage of macroalgae permit effective long time use of high alkalinity culture media with resultant high dissolved carbon concentration during which precipitation problems are avoided.

Basically, one uses temporal separation of nutrient (P,N) fertilization and growth under C enrichment. Every 1-2 weeks, the pond is drained, or drawn down, non-carbon enhanced seawater is introduced and high levels of N and K fertilizer is added. After 24 hours, this water is drained and carbon enriched seawater added and maintained until N and K fertilization is again needed. Alternatively, the crop can be moved to special fertilization ponds, using physical separation of the two processes.

In addition to Gracilaria, cultivation of other macroalgae that can be enhanced by this invention include Agardhiella, Porphyra, Gelidium, Pterodadia, Laminaria, Hypnea and Chondrus.

The embodiments of the invention in whcih an exclusive property or privilege is claimed are defined as follows:

1. In a method for the production of macroalgae in a marine culture system including, as a culture medium, an aqueous solution of salt, dissolved carbon dioxide and dissolved bicarbonate at a predetermined pH, the improvement in the manner of creating the culture medium which comprises:
    adjusting the alkalinity of a quantity of freshwater to between about 1 to 10 meq/l. by the addition thereto of an alkaline reagent selected from sodium hydroxide, potassium hydroxide and sodium carbonate or mixtures thereof,
    diluting seawater with said alkalinity adjusted freshwater to create a saline solution having a salinity of between about 15 to 25 parts per thousand and an alkalinity of between about 3 to 1 meq/l.
    dissolving carbon dioxide in the resulting solution to bring its pH to between about 7.5 and 8.5, and
    using said carbon dioxide enriched solution as said culture medium.

2. In a method for the production of macroalgae in a marine culture system including, as a culture medium, an aqueous solution of salt, dissolved carbon dioxide and dissolved bicarbonate at a predetermined pH, the improvement in the manner of creating the culture medium which comprises:
    adjusting the alkalinity of a quantity of freshwater to between about 1 to 10 meq/l. by the addition of freshwater an alkaline reagent selected from sodium hydroxide, potassium hydroxide and sodium carbonate or mixtures thereof,
    forming a charging influent for said system by diluting a volume of seawater with a volume of said alkalinity adjusted freshwater to create a desired salinity and alkalinity, dissolving carbon dioxide in the resulting influent to bring its pH to between 7.5 and 8.5, and charging the carbon dioxide enriched influent into said system.

3. A method for the culturing of macroalgae which comprises the steps:

forming a marine medium in which to conduct said culturing by diluting seawater with freshwater to a salinity of between about 15 to 25 parts per thousand, adjusting the pH of said marine medium to a pH of between about 7.5 and 8.5 and the alkalinity to between about 3 and 10 meg/l. by the addition thereto of an alkaline reagent selected from sodium hydroxide, potassium hydroxide and sodium carbonate or mixtures thereof, dissolving carbon dioxide in the resulting adjusted marine medium, charging the carbon dioxide enriched marine medium into a containing space, inoculating said charged marine medium with macroalgae of the species to be cultured, and permitting said inoculated marine medium to be exposed to sunlight whereby to grow said macroalgae species therein with enhanced productivity.

4. The method of claim 3 wherein said macroalgae is Graciliaria.

5. The method of claim 3 wherein said containing space is a terresstrial pond.

6. The method of claim 3 wherein said containing space is a tank or raceway.

* * * * *